(12) United States Patent
Okano et al.

(10) Patent No.: US 6,372,141 B1
(45) Date of Patent: Apr. 16, 2002

(54) METHOD FOR SEPARATING PTH AMINO ACIDS

(75) Inventors: Teruo Okano, Chiba-ken; Akihiko Kikuchi; Yasuhisa Sakurai, both of Tokyo; Hideko Kanazawa; Yoshikazu Matsushima, both of Kanagawa-ken, all of (JP)

(73) Assignee: Amersham Pharmacia Biotech K.K., Tokyo (JP)

( * ) Notice: Subject to any disclaimer, the term of this patent is extended or adjusted under 35 U.S.C. 154(b) by 0 days.

(21) Appl. No.: 09/355,113

(22) PCT Filed: Jan. 26, 1998

(86) PCT No.: PCT/JP98/00296

§ 371 Date: Sep. 10, 1999

§ 102(e) Date: Sep. 10, 1999

(87) PCT Pub. No.: WO98/33064

PCT Pub. Date: Jul. 30, 1998

(30) Foreign Application Priority Data

Jan. 24, 1997 (JP) .............................................. 9-011601

(51) Int. Cl.[7] .............................................. B01D 15/08
(52) U.S. Cl. ...................... 210/635; 210/656; 210/198.2
(58) Field of Search ................................. 210/635, 656, 210/198.2, 659; 530/413, 417

(56) References Cited

FOREIGN PATENT DOCUMENTS

| JP | 6 18503 | 1/1994 | .................. 210/656 |
| JP | 6331620 | 12/1994 | .................. 210/656 |
| JP | 07318551 A | 12/1995 | .................. 210/656 |

OTHER PUBLICATIONS

Strydom, *Journal of Chromatography A*, 662, pp.227–233 (1994).
Hayakawa et al., *Journal of Chromatography*, 487 pp. 161–166 (1989).
Glajch et al., *Journal of Chromatographic Science*, vol. 25, pp.4–11 (Jan. 1987).
Ashman et al., *FEBS Letters*, vol. 190, No. 1, pp.129–132 (Oct. 1985).
Kim, *Journal of Chromatography*, 247, pp.103–110 (1982).
Annan, *Journal of Chromatography*, 173, pp.194–197 (1979).
Vries et al., *FEBS Letters*, vol. 55, No. 1, pp. 65–67 (Jul. 1975).
Matthews et al., *Journal of Chromatography*, 110, pp.369–373 (1975).
Akira Hosoya et al., "Control of Selectivity for Separation in HPLC using New Temperature–Responsive High–Molecular–Weight Filler (in Japanese)" Chromatography, 14(5), pp. 122–123 (1993) (English abstract).
Kanazawa. et al., Temperature–Responsive Liquid Chromatography Using Poly(N–isopropylacrylamide)–Modified Silica, Anal. Chem., 68(1), pp. 100–105 (1996).
Kanazawa et al., Temperature–Responsive Liquid Chromatography. 2. Effects of Hydrophobic Groups in N–Isopropylacrylamide Copolymer–Modified Silica, Anal. Chem., 69, pp. 823–830 (1997).

*Primary Examiner*—Ernest G. Therkorn
(74) *Attorney, Agent, or Firm*—Birch, Stewart, Kolasch & Birch, LLP

(57) ABSTRACT

PTH-amino acids can be analyzed within a short time at a high sensitivity by chromatographically separating said PTH-amino acids with the use of a packing wherein the hydrophilic/hydrophobic balance on the stationary phase surface can be changed by an external signal while fixing the mobile phase to an aqueous system.

7 Claims, 5 Drawing Sheets

METHOD FOR SEPARATING PTH AMINO ACIDS

This application is the national phase under 35 U.S.C. §371 of PCT International Application No. PCT/JP98/00296 which has an International filing date of Jan. 26, 1998 which designated the United States of America.

TECHNICAL FIELD

This invention relates to a novel method for chromatographically separating PTH-amino acids (i.e., 3-phenyl-2-thiohydantoin derivatives of amino acids) by changing the hydrophilic/hydrophobic balance on the stationary phase surface in an aqueous system by an external signal (for example, temperature).

BACKGROUND ART

Amino acid sequences of proteins, peptides, etc. are determined by the Edman degradation method which comprises successively, from the terminal, liberating amino acid residues each as anilinothiazolinone, and then converting it into a stable phenylthiohydantoin derivative (PTH-amino acid) under acidic conditions followed by identification. In the identification, it has been a practice to use liquid chromatography with the use of a reversed phase column. By using the reversed phase column, all of 20 amino acid species constituting proteins can be separated from each other by a single analytical operation and analyzed within 1 hour at a relatively high sensitivity.

There are marketed various reversed phase columns wherein porous silica gel is employed as the stationary phase. On the silica gel, octadecylsilane group, phenyl group, etc. are fixed by chemical bonds thereby making the surface of the silica carrier hydrophobic. On the surface of this reversed phase, various PTH-amino acids are separated from each other due to the difference in the degree of hydrophobicity. As the chromatographic eluting solution, use is made of a mixture of a buffer solution with an organic solvent miscible with water.

PTH-amino acids may be eluted by continuously increasing the organic solvent concentration in the mobile phase. Alternatively, it may be eluted at a constant organic solvent concentration. In either case, elution is performed by changing the hydrophobicity or hydrophilicity of the eluting solvent. As the buffer solution, sodium acetate-based ones and ammonium acetate-based ones are mainly employed. As the organic solvent, acetonitrile and methanol are mainly employed. The separating ability widely varies depending on various separation conditions such as the flow rate of the elution solvent, ionic strength, pH, column temperature, etc. In general, separation at a higher temperature can give the more favorable results, though the performance varies from column to column. The PTH-amino acids thus separated are detected with an UV detector at a wavelength of, for example, 254 nm or 268 nm and then identified by comparing in elution time with standard PTH-amino acids.

However, the organic solvents and buffer solutions employed as the conventional mobile phases contaminate the eluates and bring about extremely strong UV absorption. Thus, there arises a problem that the stability of a base line and sensitivity are seriously lowered thereby. Moreover, the column should be washed and equilibrated with the initial eluting solution before starting continuous analysis, which brings about another problem, i.e., a prolonged analysis time. In addition, it is feared that these organic solvents and buffer solutions would induce environmental pollution. Accordingly, it has been required to establish a separation method without resort to these substances.

To solve the above-described problem, JP (Kokai) Hei 7-318551 proposes a chromatographic method with the use of a chromatographic packing capable of separating or purifying biological factors (proteins, DNAs, saccharides, lipids, etc.) or cells by regulating the interaction of these substance with the surface of a solid in an aqueous system by an external signal (for example, temperature). By using this method, biological factors or cells can be separated or purified by regulating the surface characteristics of the stationary phase under a temperature change while fixing the mobile phase to an aqueous system without resort to any organic solvent or buffer solution as the mobile phase. Thus, the biological factors (proteins, etc.) or cells can be separated and collected while sustaining the functions thereof in a single aqueous mobile phase, thus preventing the contamination with impurities.

However, the solutes which can be separated or purified by the method reported by JP (Kokai) Hei 7-318551 are physiologically active proteins, cells and the like. More particularly, the above patent discloses exclusively bovine serum albumin, IgG, fibrinogen, fibronectin, transferrin, blood coagulation factor, etc. (see, for example, page 5, column 7, lines 5–10 in the official gazette thereof). Namely, no other substance is stated therein.

DISCLOSURE OF THE INVENTION

To develop a method for analyzing PTH-amino acids within a short time at a high sensitivity, the present inventors have conducted intensive studies. As a result, they have found a fact, as an unexpected turn even for a person skilled in the art, that PTH-amino acids can be analyzed by using the method described in JP (Kokai) Hei 7-318551, though free amino acids cannot be analyzed thereby. The present invention has been completed based on this finding.

Accordingly, the present invention provides a method for separating PTH-amino acids characterized by chromatographically separating said PTH-amino acids with the use of a packing wherein the hydrophilic/hydrophobic balance on the stationary phase surface can be changed by an external signal while fixing the mobile phase to an aqueous system.

The present invention further provides a method for separating PTH-amino acids characterized by comprising retaining said PTH-amino acids by a stationary phase comprising a chromatographic packing chemically modified with a polyalkylacrylamide having terminal amino, carboxyl, hydroxyl groups, etc. or a copolymer of the same; and allowing the PTH-amino acids to pass through a single mobile phase while changing the hydrophilic/hydrophobic balance on the stationary phase surface by the temperature gradient method wherein the external temperature is changed stepwise to thereby separate the PTH-amino acids.

BEST MODE FOR CARRYING OUT THE INVENTION

Figure 1:
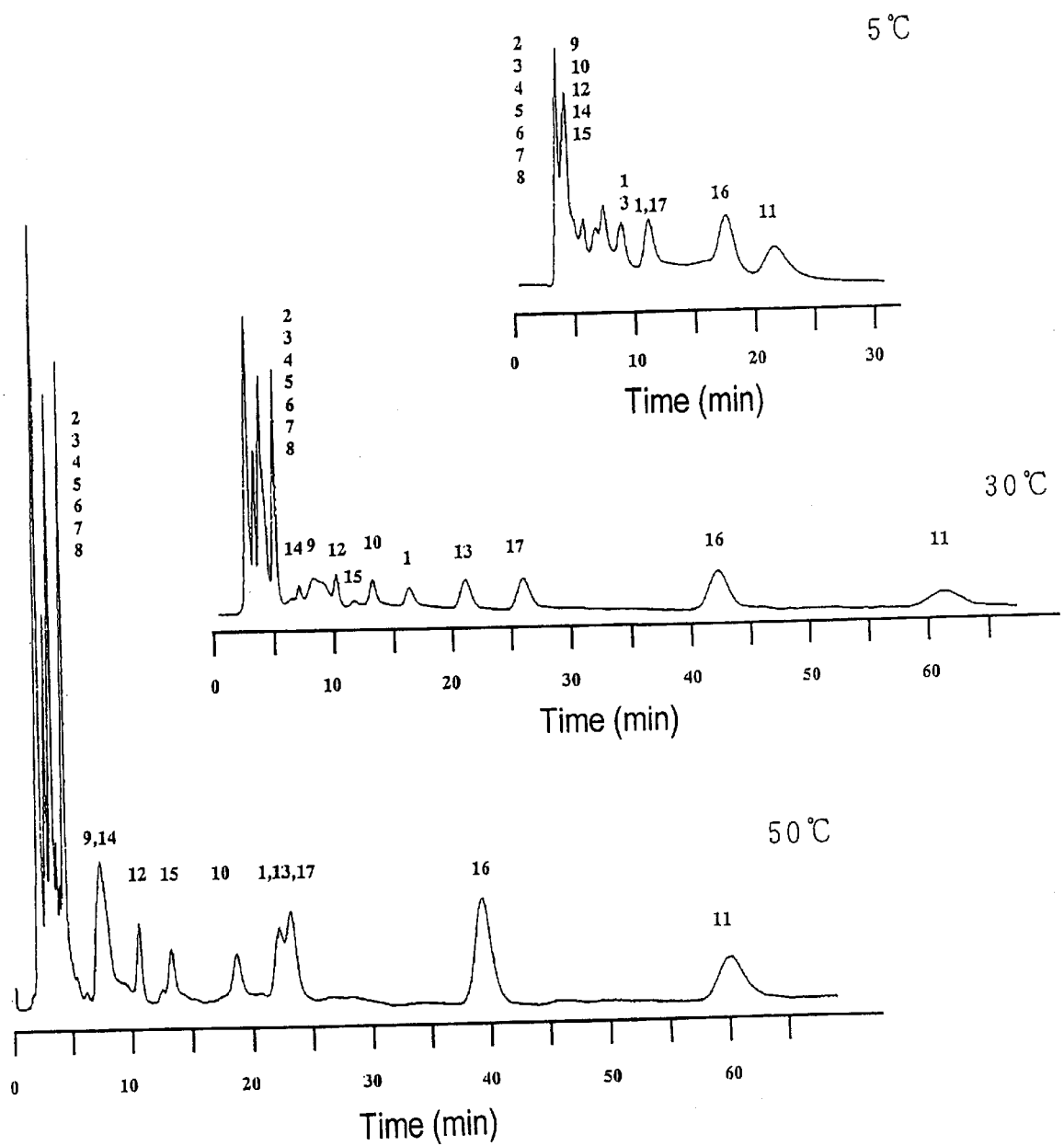
FIG. 1 provides a chart showing the analytical data of 17 PTH-amino acids obtained by the separation method described in Example 1.

The PTH-amino acids to be separated by the method according to the present invention are not restricted. Namely, any PTH-amino acids may be used therefor.

The aqueous system to be used in the method of the present invention involves water alone or aqueous solutions containing inorganic salts but free from organic solvent. In this definition, water means distilled water, deionized water or both.

The external change to be used in the method according to the present invention is exemplified by a temperature change. To change the hydrophilic/hydrophobic balance on the stationary phase surface by changing temperature, a temperature-responsive polymer may be introduced into the surface of the carrier of the chromatographic packing. Examples of packings of this type include chromatographic packings chemically modified on the surface of the carrier with polyalkylacrylamides having terminal amino, carboxyl, hydroxyl groups, etc. or copolymers thereof. These chemically modified packings are exemplified by silica carriers having functional groups (amino, carboxyl, hydroxyl groups, etc.) on the surface chemically modified with the above-mentioned polyalkylacrylamides or copolymers thereof. Particular examples of the silica carriers having functional groups (amino, carboxyl, hydroxyl groups, etc.) include aminopropyl silica gel, Aminosephadex, ion exchange resins, etc.

It is preferable that the polyalkylacrylamide to be used in the method according to the present invention is selected from among poly(N-isopropylacrylamide), polydiethylacrylamide and polyacryloylpyrrolidine represented by the following formula, and copolymers of the constitutional units of these polymers with alkyl acrylates or alkyl methacrylates.

Polyalkylacrylamide:

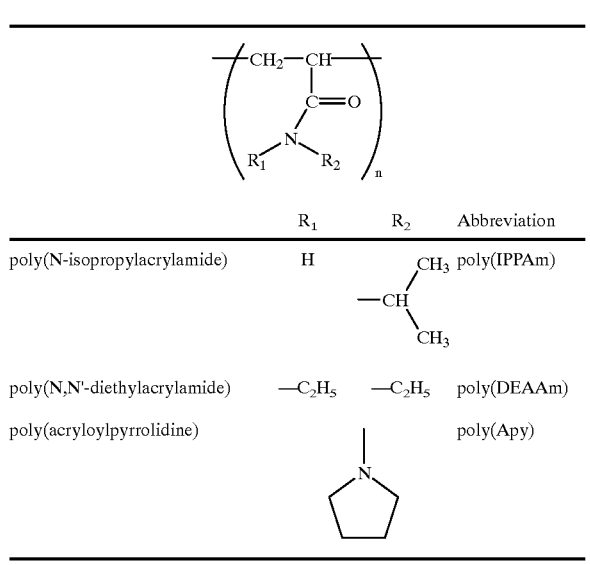

Copolymer:

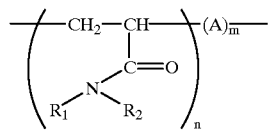

A: content: 50–60%

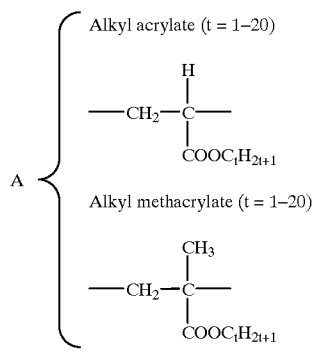

Since poly(N-isopropylacrylamide) (PIPAAm) has a lower limit critical temperature of 32° C., a carrier chemically modified therewith undergoes a large change in the hydrophilic/hydrophobic surface properties at this critical temperature. When the surface of a chromatographic packing is grafted or coated with this polymer, the power of retaining a sample varies depending on temperature. Thus, the retention behavior can be regulated by controlling temperature without changing the composition of the eluting solution. A lower limit critical temperature of 32° C. or above can be achieved by copolymerizing N-isopropylacrylamide with comonomers which are more hydrophilic than isopropylacrylamide, for example, acrylamide, methacrylic acid, acrylic acid, dimethylacrylamide and vinyl pyrrolidone. On the other hand, a lower limit critical temperature lower than 32° C. can be achieved by copolymerizing the N-isopropylacrylamide with hydrophobic comonomers, for example, styrene, alkyl methacrylate and alkyl acrylate.

The lower limit critical temperature of polydiethylacrylamide is about 30 to 32° C. At this temperature, this polymer undergoes a change in the surface hydrophilic/hydrophobic nature. Similar to the above-mentioned case of poly(N-isopropylacrylamide), the power of retaining a sample can be thus regulated by controlling temperature. The novel chromatographic carrier to be used in the present invention is prepared by chemically modifying or coating the carrier with a polymer. The chemical modification can be carried out by two methods, i.e., surface grafting and radical polymerization. In the case of coating, on the other hand, the polymer is insolubilized within the application temperature range and then the insolubilized product is employed in coating.

As described above, surface grafting and radical polymerization can be employed as the chemical modification means by which a temperature-responsive polymer is introduced into a carrier. In the surface grafting method, a temperature-responsive polymer of a definite size is first synthesized and then grafted to the carrier. In the radical polymerization method, in contrast thereto, monomer(s) are polymerized on the surface of the carrier to give a polymer.

Compared with the surface grafting method, the radical polymerization method makes it possible to introduce the temperature-responsive polymer into the surface of the carrier at a high density. Thus, the hydrophobicity of the surface of the carrier can be elevated and the retention time can be easily controlled. In this case, moreover, non-specific adsorption on the carrier surface due to the interaction with silica gel can be easily suppressed.

EXAMPLES

To further illustrate the present invention in greater detail, and not by way of limitation, the following Examples will be given.

Example 1

Synthesis of Polymer

An IPAAm copolymer having a terminal carboxyl group was synthesized in such a manner as to give a molecular weight of 4,000 as a standard. The molecular weight of the polymer can be designed by controlling the amount of 3-mercaptopropionic acid (MPA) employed as a chain transfer agent. To prepare a copolymer having a molecular weight of 4,000 based on the data given in literatures, the amount of MPA was regulated to give a molar ratio MPA/(IPAAm+RMA) of 0.028.

Purified monomer (IPAAm: 25.0 g).

Hydrophobic monomer (1% by mol of BMA based on IPAAm: 0.313 g, 3% of BMA: 0.972 g, 5% of BMA: 1.653 g, 1% of HMA: 0.38 g).

Radical polymerization initiator (MPA, 1% of BMA: 0.662 g, 3% of BMA: 0.677 g, 5% of BMA: 0.691 g, 1% of HMA: 0.663 g).

DMF (50 ml).

NOTE: In the above composition, each abbreviation has the following meaning:

IPAAm: N-isopropylacrylamide.
BMA: n-butyl methacrylate.
AIBN: 2,2'-azobis(isobutyronitrile).
HMA: n-hexyl methacrylate.
MPA: 3-mercaptopropionic acid.
DMF: N,N-dimethylformamide.

The above components were fed into a polymerization tube and fixed with a rubber ring provided with a three-way stopcock. The polymerization tube was introduced into liquid nitrogen, while closing the cock, and completely frozen. Next, the cock was opened and the contents of the tube were degassed by using a vacuum pump. After closing the cock again, the polymerization tube was introduced into methanol and the sample in the tube was completely dissolved. This procedure was repeated thrice (freezing/thawing degassing method). Then the polymerization tube containing the completely degassed sample under reduced pressure was introduced into a thermostat under shaking at 70° C. and radical polymerization was performed for 2 hours to thereby synthesize a copolymer having a carboxyl group at one end. After the completion of the reaction, the reaction mixture was cooled to room temperature by allowing to stand. Then the solvent (DMF) was concentrated by distilling at 40° C. under reduced pressure and the residue was dropped into ice-cooled diethyl ether to thereby give a polymer. The polymer thus obtained was taken up by filtration and dried at ordinary temperature under reduced pressure overnight. The dried product was dissolved in acetone and purified again with diethyl ether. The polymer thus obtained was taken up again by filtration and dried at ordinary temperature under reduced pressure overnight. The obtained polymer was then dissolved to give a 5% solution. Next, it was dialyzed with the use of a dialysis membrane while replacing water frequently. After the completion of the dialysis, the solution was transferred into an appropriate container and freeze-dried in a freeze-dryer for 2 days to thereby give a copolymer having a further elevated purity.

Introduction of IPAAm Copolymer into Carrier

<Active esterification (succinylation) method>

| | |
|---|---|
| Copolymer synthesized above | 1 molar eq. |
| DCC | 2.5 molar eq. |
| N-hydroxysuccinimide | 2.5 molar eq. |
| ethyl acetate | 100 ml. |

1. The synthetic copolymer was fed into a round-bottomed flask and dissolved in a half amount of ethyl acetate.

2. N-Hydroxysuccinimide was added thereto. Next, DCC (dicyclohexylcarbodiimide) was weighed into a sample bottle, dissolved in the residual ethyl acetate and then added to the above mixture.

3. The obtained mixture was immersed in ice-water at 4° C. and stirred with a stirrer for 2 hours. Then it was introduced into a thermostat at 25° C. and stirred therein overnight.

4. The solution was filtered to thereby remove dicyclohexyl urea formed as a by-product followed by concentration under reduced pressure.

5. Finally, the residue was purified with diethyl ether. The product thus formed was taken up by filtration and dried under reduced pressure. The succinylated copolymer thus obtained was stored in a freezer.

Bonding to Carrier (silica gel)

The succinylated copolymer was reacted in three portions with aminopropyl silica gel with the use of 1,4-dioxane as a solvent. The reaction was carried out at room temperature (25° C.).

1. The succinylated copolymer (1.5 g) was dissolved in 1,4-dioxane (50 ml) and reacted with aminopropyl silica gel (3 g) in a thermostat under shaking overnight.

2. The precipitate obtained by filtering the above liquid reaction mixture was combined with another portion (1.5 g) of the copolymer and dissolved again in 1,4-dioxane (50 ml). Then the reaction was carried out overnight. This procedure was repeated twice.

3. The precipitate obtained by the final filtration was thoroughly washed with methanol (500 ml), distilled water (1 l) and ultra-pure water (500 ml), then dried under reduced pressure and stored in a desiccator as a packing.

PREPARATION OF SAMPLES

Sample A

17 PTH-amino acids were dissolved in distilled water to give 10 ml of a PTH-amino acid mixture having the concentrations as specified below.

|   |                              |                |
|---|------------------------------|----------------|
| 1. | PTH-L-arginine hydrochloride | 1.000 mg/ml.  |
| 2. | PTH-L-asparagine             | 0.404 mg/ml.  |
| 3. | PTH-L-aspartic acid          | 1.084 mg/ml.  |
| 4. | potassium PTH-L-cystate      | 1.000 mg/ml.  |
| 5. | PTH-L-citrulline             | 0.001 mg/ml.  |
| 6. | PTH-L-glutamine              | 0.124 mg/ml.  |
| 7. | PTH-L-glutamic acid          | 0.471 mg/ml.  |
| 8. | PTH-glycine                  | 0.103 mg/ml.  |
| 9. | PTH-L-histidine hydrochloride| 1.000 mg/ml.  |
| 10.| PTH-L-leucine                | 0.014 mg/ml.  |
| 11.| PTH-L-lysine                 | 0.005 mg/ml.  |
| 12.| PTH-DL-methionine            | 0.063 mg/ml.  |
| 13.| PTH-L-phenylalanine          | 0.038 mg/ml.  |
| 14.| PTH-L-proline                | 0.038 mg/ml.  |
| 15.| PTH-Δ-threonine              | 0.019 mg/ml.  |
| 16.| PTH-DL-tryptophan            | 0.019 mg/ml.  |
| 17.| PTH-L-tyrosine               | 0.077 mg/ml.  |

Sample B

20 PTH-amino acids were dissolved in distilled water to give 10 ml of a PTH-amino acid mixture having the concentrations as specified below.

|   |                              |                |
|---|------------------------------|----------------|
| 1. | PTH-DL-α-alanine             | 0.423 mg/ml.  |
| 2. | PTH-L-arginine hydrochloride | 1.000 mg/ml.  |
| 3. | PTH-L-asparagine             | 0.404 mg/ml.  |
| 4. | PTH-L-aspartic acid          | 1.084 mg/ml.  |
| 5. | potassium PTH-L-cystate      | 1.000 mg/ml.  |
| 6. | PTH-L-glutamine              | 0.124 mg/ml.  |
| 7. | PTH-L-glutamic acid          | 0.471 mg/ml.  |
| 8. | PTH-glycine                  | 0.103 mg/ml.  |
| 9. | PTH-L-histidine hydrochloride| 1.000 mg/ml.  |
| 10.| PTH-L-isoleucine             | 0.006 mg/ml.  |
| 11.| PTH-L-leucine                | 0.014 mg/ml.  |
| 12.| PTH-L-lysine                 | 0.005 mg/ml.  |
| 13.| PTH-DL-methionine            | 0.063 mg/ml.  |
| 14.| PTH-L-phenylalanine          | 0.038 mg/ml.  |
| 15.| PTH-L-proline                | 0.038 mg/ml.  |
| 16.| PTH-DL-serine                | 0.553 mg/ml   |
| 17.| PTH-Δ-threonine              | 0.019 mg/ml.  |
| 18.| PTH-DL-tryptophan            | 0.019 mg/ml.  |
| 19.| PTH-L-tyrosine               | 0.077 mg/ml.  |
| 20.| PTH-DL-valine                | 0.024 mg/ml.  |

Sample C

14 PTH-amino acids were dissolved in distilled water to give 10 ml of a PTH-amino acid mixture having the concentrations as specified below.

|   |                              |                |
|---|------------------------------|----------------|
| 1. | PTH-L-aspartic acid          | 1.084 mg/ml.  |
| 2. | PTH-L-glutamic acid          | 0.471 mg/ml.  |
| 3. | PTH-L-asparagine             | 0.404 mg/ml.  |
| 4. | PTH-L-glutamine              | 0.124 mg/ml.  |
| 5. | PTH-L-histidine hydrochloride| 1.000 mg/ml.  |
| 6. | PTH-DL-α-alanine             | 0.423 mg/ml.  |
| 7. | PTH-L-arginine hydrochloride | 1.000 mg/ml.  |
| 8. | PTH-L-proline                | 0.038 mg/ml.  |
| 9. | PTH-DL-methionine            | 0.063 mg/ml.  |
| 10.| PTH-Δ-threonine              | 0.019 mg/ml.  |
| 11.| PTH-L-leucine                | 0.014 mg/ml.  |
| 12.| PTH-L-phenylalanine          | 0.038 mg/ml.  |
| 13.| PTH-L-tyrosine               | 0.077 mg/ml.  |
| 14.| PTH-DL-tryptophan            | 0.019 mg/ml.  |

Separation of PTH-amino Acids Contained in
Sample A

100 μl of the sample A was poured into a column packed with the above-mentioned packing (silica modified by PIPAAm-MA 5%). The column was connected to high performance liquid chromatograph (HPLC) and separation was carried out by using distilled water as an eluting solution at a flow rate of 1.0 mg/min. Detection was performed at a wavelength of 254 nm with the use of an ultraviolet/visible photometric detector. The column was located in a thermostat and the column temperature was changed to thereby compare the separating abilities. Poly(N-isopropylacrylamide) undergoes a change in the hydrophobic/hydrophilic nature on the carrier surface at 32° C. As described above, this temperature is called the lower limit critical temperature. At 5° C. lower than the lower limit critical temperature, PTH-L-lysine showing the longest retention time (peak 11 in FIG. 1) showed a retention time of 22 minutes. At 30° C., PTH-L-lysine showed a retention time of 61 minutes (FIG. 1). Thus, it was confirmed that the elution time could be changed by changing the column temperature to thereby alter the hydrophobic/hydrophilic nature on the carrier surface.

Example 2

Separation of PTH-amino Acids Contained in
Sample B

20 PTH-amino acids contained in the sample B were separated under the same conditions as those employed in Example 1 to separate the PTH-amino acids contained in the sample A.

Example 3

Separation of PTH-amino Acids Contained in
Sample C

Figure 2:
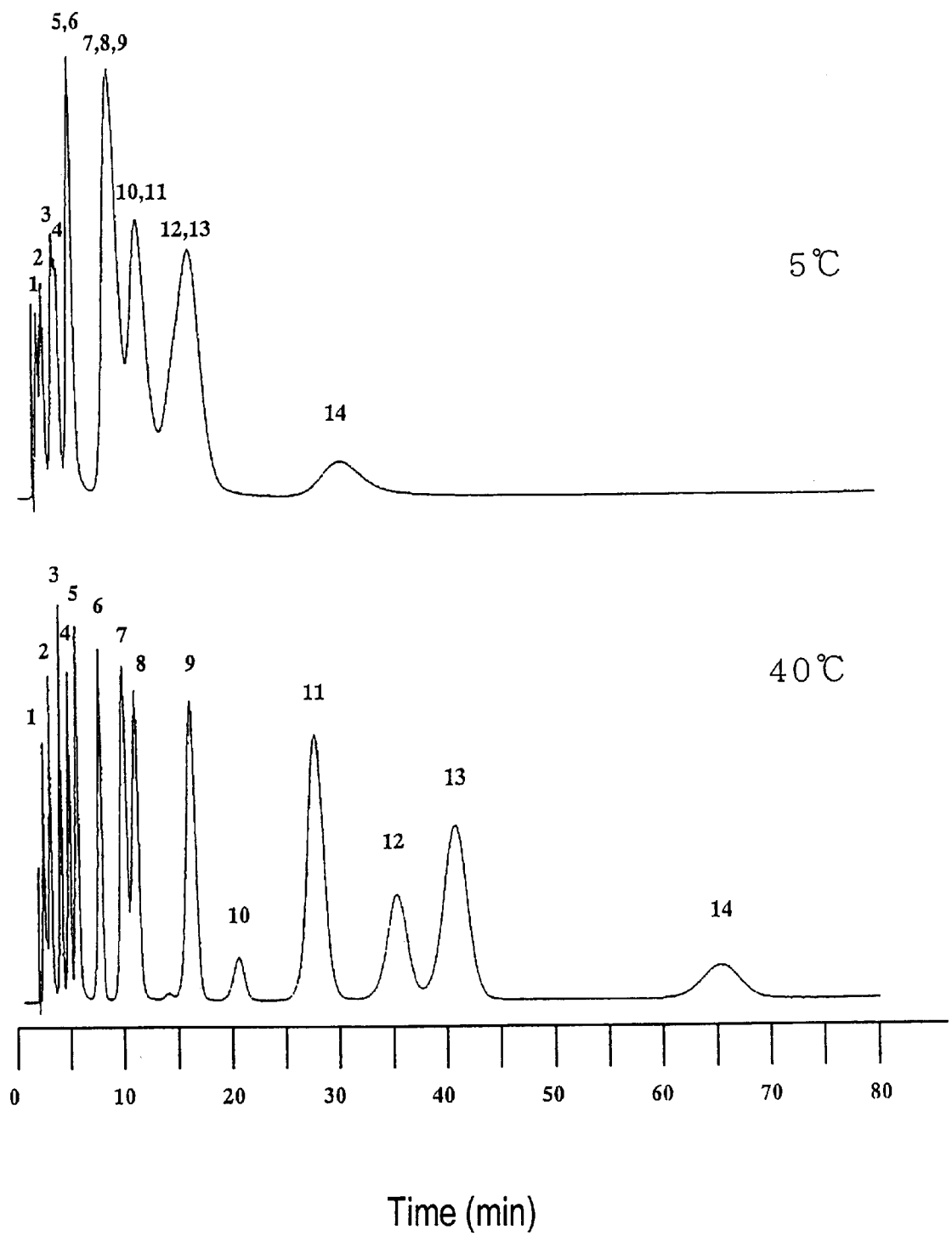
FIG. 2 provides a chart showing the analytical data of 14 PTH-amino acids obtained by the separation method described in Example 3.

Silica grafted with poly(N-isopropylacrylamide) gel (poly(IPAAm) gel-graft silica) was prepared in accordance with the methods (a) to (d) described in JP (Kokai) Hei 7-318551. Then 50 μl of the sample C was poured into a column packed with the above-mentioned silica packing. The column was connected to high performance liquid chromatograph and separation was carried out by using a 0.5 M aqueous solution of sodium chloride as an eluting solution at a flow rate of 1.0 mg/min. Detection was performed at a wavelength of 254 nm with the use of an ultraviolet/visible photometric detector. The column was located in a thermostat and the column temperature was set to 5° C. and 40° C. to thereby compare the separating abilities. FIG. 2 shows the results.

As FIG. 2 clearly shows, 14 PTH-amino acids could be hardly separated at a column temperature of 5° C. At 40° C. exceeding the lower limit critical temperature, the carrier surface became hydrophobic and thus interactions on the hydrophobic surface were strengthened. As a result, the retention time of each amino acid was prolonged, thereby enabling the separation. Thus, the physical nature on the carrier surface can be regulated by controlling the column temperature, which makes it possible to determine the optimum separation conditions. Since the lower limit critical temperature can be regulated by controlling the amount of the N,N-dimethylacrylamide monomer to be copolymerized with the N-isopropylacrylamide monomer, a temperature-responsive polymer showing the phase transition at an arbitrary temperature can be synthesized.

As FIG. 2 shows, it took 65 minutes to complete the analysis at 40° C. However, the separation time can be further shortened by performing the separation under temperature gradient.

Example 4

Figure 3:
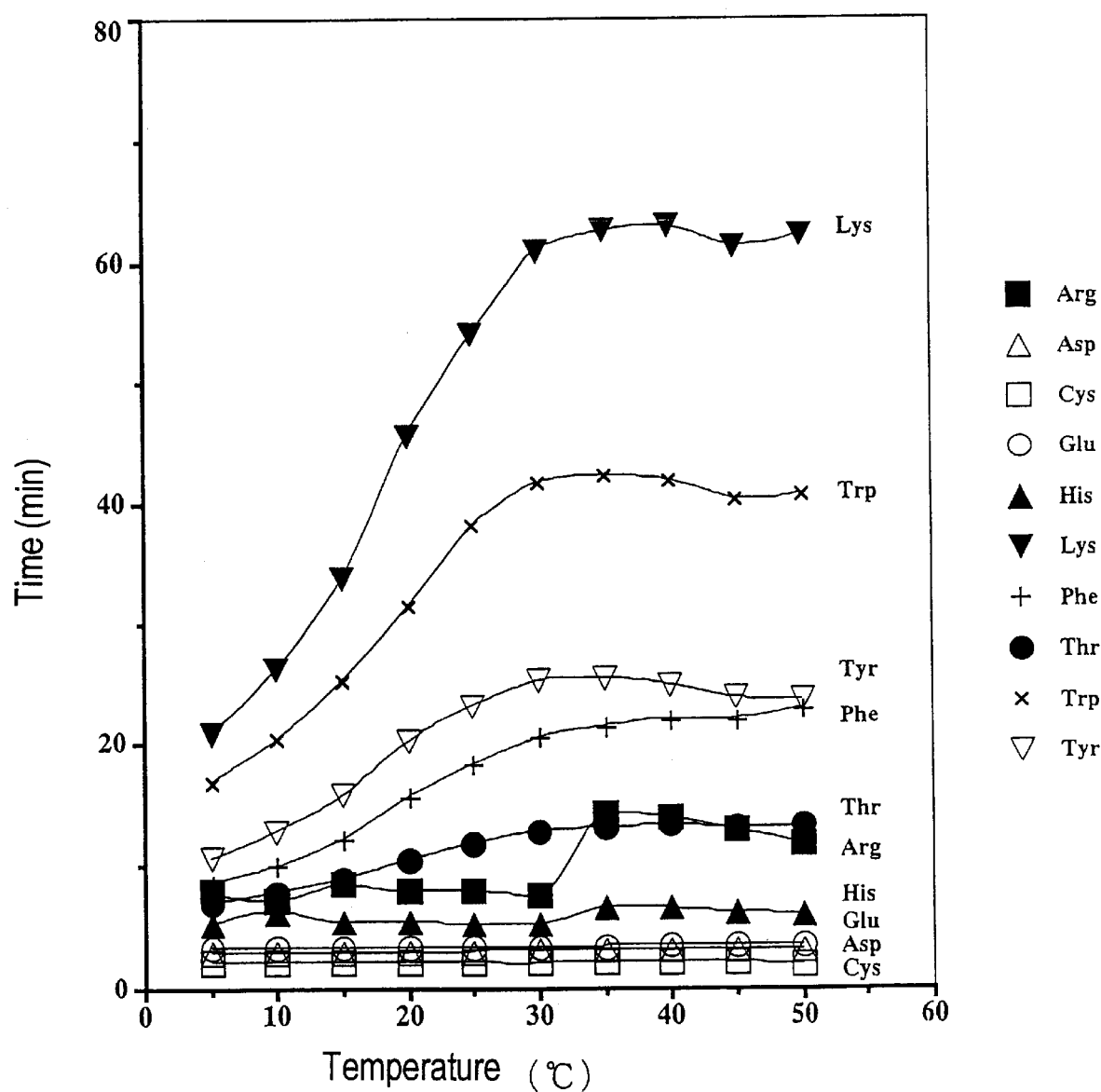
FIG. 3 provides a graph showing the relationship between temperature and retention time of 10 PTH-amino acids, among 20, employed in Example 4.
Figure 4:
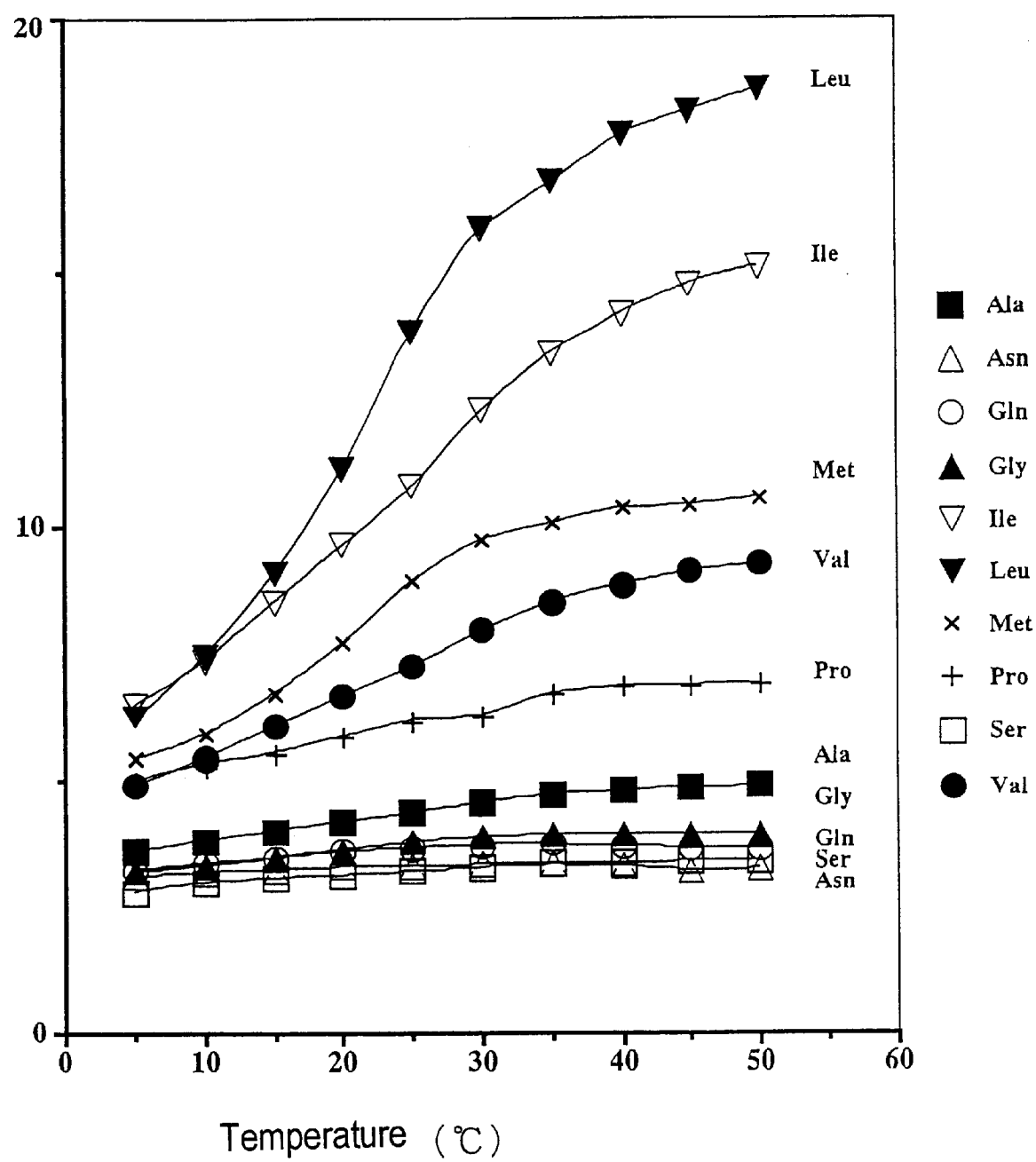
FIG. 4 provides a graph showing the relationship between temperature and retention time of the residual 10 PTH-amino acids not shown in FIG. 3.

Discussion on the Relation Between Temperature
and Retention Time of PTH-amino Acid The amino acids contained in the sample B were separated under the same conditions as those employed in Example 1 to separate the PTH-amino acids contained in the sample A to examine the relationship between the temperature and retention time of each PTH-amino acid. The column temperature was varied in 10 grades, i.e., 5° C., 10° C., 15° C., 20° C., 25° C., 30° C., 35° C., 40° C., 45° C. and 50° C. and the retention time of each PTH-amino acid was measured at each column temperature. FIGS. 3 and 4 show the results.

FIGS. 3 and 4 prove that hydrophobic amino acids showing a large change in the elution time due to a temperature change could be separated from polar amino acids showing little change, excluding PTH-lysine. That is to say, the optimum separation conditions can be easily determined by setting the column temperature to appropriate levels.

Example 5

Formation of Gel Layer on Aminopropylsilica Surface by Radical Polymerization

1) Introduction of Polymerization Initiator into Aminopropyl Silica

Aminopropyl silica (5 g) serving as the carrier in the packing was reacted in DMF with an azo-type polymerization initiator 4,4'-azobis(4-cyanopentanoic acid) (V-501; 3.5 g (12.5 mmol)) having carboxyl groups at both ends with the use of N-ethoxycarbonyl-2-ethoxy-1,2-dihydroquinoline (EEDQ: 6.18 g (25.0 mmol)) as a condensing agent under a nitrogen atmosphere for 6 hours at room temperature. Thus, the polymerization initiator V-501 was introduced into the aminopropyl silica and fixed thereto via amide bonds.

2) Formation of Surface Gel Layer 4 g of the silica having V-501 fixed thereto, prepared in the above 1), was copolymerized with isopropylacrylamide (IPAAm: 10 g) and N,N'-methylene-bis(acrylamide) (0.27 g) in ethanol under a nitrogen atmosphere at 70° C. for 5 hours, thus forming a gel layer on the carrier surface. The obtained carrier (gel (IPAAm-2% BIS) silica) was employed as a packing in the subsequent procedures.

Preparation of Sample 10 ml of a PTH-amino acid mixture containing 6 PTH-amino acids as specified below was prepared.

| | |
|---|---|
| 1. PTH-L-glutamine | 0.124 mg/ml. |
| 2. PTH-L-glycine | 0.103 mg/ml. |
| 3. PTH-DL-α-alanine | 0.423 mg/ml. |
| 4. PTH-DL-methionine | 0.063 mg/ml. |
| 5. PTH-L-leucine | 0.014 mg/ml. |
| 6. PTH-L-tyrosine | 0.077 mg/ml. |

Separation of PTH-amino Acids Contained in Sample

Figure 5:
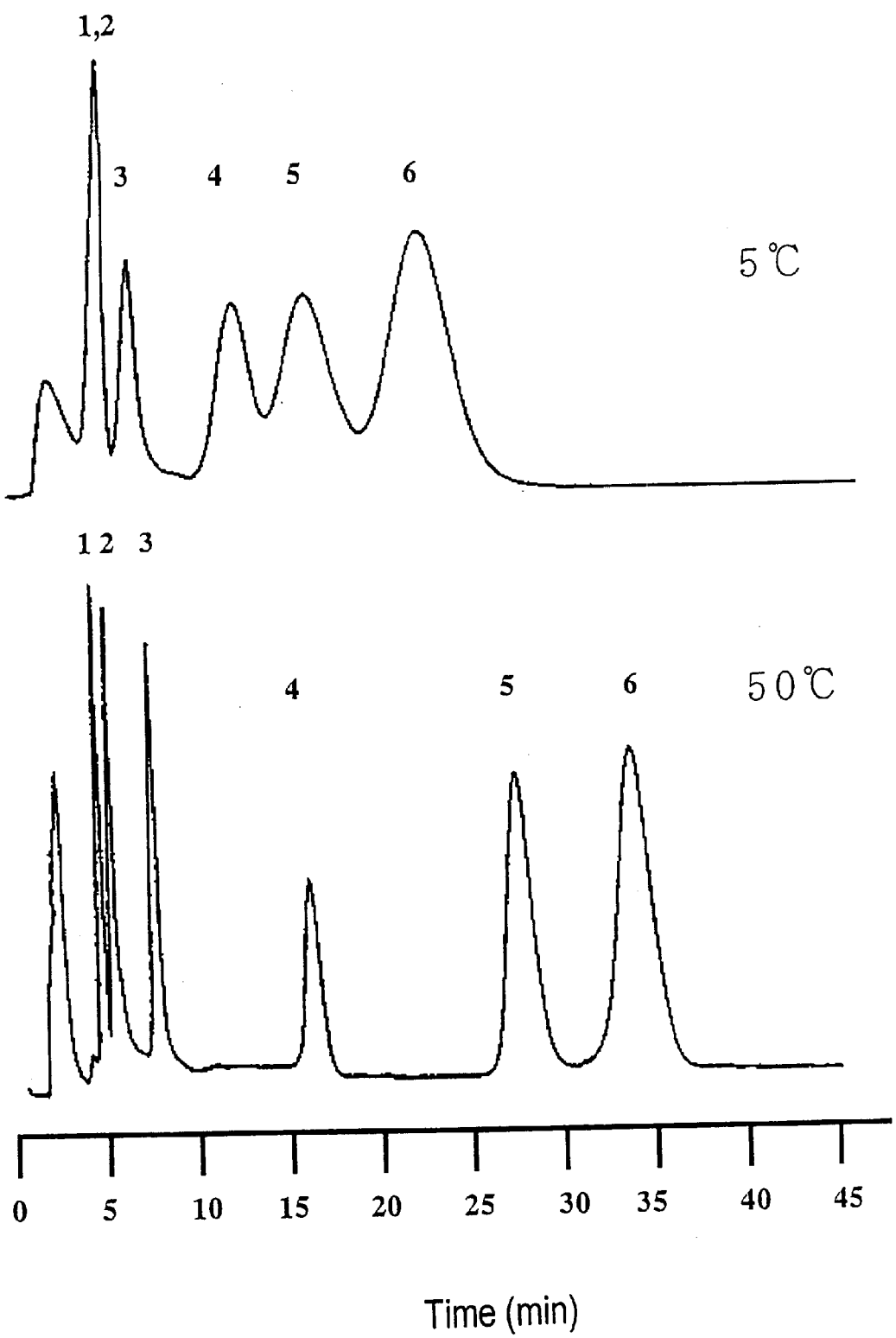
FIG. 5 provides a chart showing the analytical data of 6 PTH-amino acids obtained by the separation method described in Example 5.

50 μl of the above sample was poured into a column packed with the above-mentioned packing (gel (IPAAm-2% BIS) silica). The column was connected to high performance liquid chromatograph and separation was carried out by using distilled water as an eluting solution at a flow rate of 1.0 mg/min. Detection was performed at a wavelength of 254 nm with the use of an ultraviolet/visible photometric detector. The column was located in a thermostat and the column temperature was set to 5° C. and 50° C. to thereby compare the separating abilities. FIG. 5 shows the results.

As FIG. 5 clearly shows, the PTH-amino acids could be easily separated by using the carrier chemically modified by radical polymerization. The retention times could be controlled depending on temperature. In this case, a large amount of a temperature-responsive polymer could be introduced into a carrier and the retention time could be prolonged, thus achieving an improved performance of separating amino acids, compared with a carrier synthesized by the surface grafting method. Reasons therefor are seemingly as follows.

In the surface grafting method, a temperature-responsive polymer of a definite size is first synthesized and then grafted to the carrier. In the radical polymerization method, in contrast thereto, monomer(s) are polymerized on the surface of the carrier to give a polymer. Compared with the surface grafting method, the radical polymerization method makes it possible to introduce the temperature-responsive polymer into the surface of the carrier at a high density. Thus, the hydrophobicity of the surface of the carrier can be elevated and the retention time can be easily controlled. In this case, moreover, non-specific adsorption on the carrier surface due to the interaction with silica gel can be easily suppressed.

INDUSTRIAL APPLICABILITY

As discussed above in detail, the method for separating PTH-amino acids according to the present invention is advantageous in the following points.

(1) Separation can be performed by using an aqueous system alone as the mobile phase without resort to any organic solvent (acetonitrile, methanol, etc.).

(2) The mobile phase can be easily prepared.

(3) Since neither any organic solvent nor buffer solution is employed, eluates are little contaminated and a stale base line can be detected, thereby enabling highly sensitive detection.

(4) Since no organic solvent is employed, the system is free from any change in the composition due to the contamination with organic solvents caused by degassing.

(5) The separation can be achieved at a high reproducibility.

For example, reproducibilities shown in the following table were obtained.

TABLE 1

| | Retention time (min) | CV |
|---|---|---|
| PTH-methionine (Met) | 9.686 | 0.057 |
| PTH-leucine (Leu) | 16.894 | 0.067 |
| PTH-tryptophan (Trp) | 37.814 | 0.058 |
| PTH-lysine (Lys) | 57.608 | 0.053 |

(Measured at 50° C.)

PTH-methionine (5 μl), PTH-leucine (10 μl), PTH-tryptophan (20 μl) and PTH-lysine (100 μl) were poured, each 5 times, into a high performance liquid chromatograph connected to a column packed with the above-mentioned packing (gel (IPAAm) silica) and the retention time of each case was measured at a column temperature of 50° C. Thus the coefficient of variation (CV) was calculated and the reproducibility was discussed. In the chromatography, water was employed as an eluting solution at a flow rate of 1.0 ml/min and each PTH-amino acid was detected by measuring the UV absorption at 254 nm. ② Method for calculating CV Each sample was measured 5 times under definite conditions (temperature, amount of the poured sample). By using the thus obtained data, the arithmetic mean and the standard deviation were determined. Then the CV was calculated in accordance with the following formulae.

$$CV = s/x \times 100 (\%)$$

$$s = \sqrt{\frac{\sum\limits_{i=1}^{n}(xi-x)^2}{n-1}}$$

x: Arithmetic mean.
xi: Determination
s: Standard deviation.
CV: coefficient of variation.

(6) retention time can be freely controlled by regulating temperature and thus the separation accuracy can be regulated.

(7) the carrier can be repeatedly employed by regulating temperature without any need for regeneration.

What is claimed is:

1. A method for separating PTH-amino acids comprising the steps of:

contacting a mobile phase comprising said PTH-amino acids with a packing, and adjusting the temperature of said stationary packing if necessary to influence the hydrophilic/hydrophobic balance on the stationary packing surface by a temperature change with the mobile phase being fixed to an aqueous system which involves water alone or aqueous solution containing inorganic salts but free from organic solvent, to thereby chromatographically separate said PTH-amino acids.

2. The method for separating PTH-amino acids as claimed in claim 1, wherein said packing is a chromatographic packing wherein the surface of a carrier is chemically modified with a temperature-responsive polymer.

3. The method for separating PTH-amino acids as claimed in claim 2, wherein said packing is a chromatographic packing wherein the surface of a carrier is chemically modified with a temperature-responsive polymer by using the radical polymerization method.

4. The method for separating PTH-amino acids as claimed in claim 2, wherein said temperature-responsive polymer is a polyalkylacrylamide having terminal amino, carboxyl, hydroxyl groups, or a copolymer of the same.

5. The method for separating PTH-amino acids as claimed in claim 4, wherein said polyalkylacrylamide is one selected from among poly(N-isopropylacrylamide), polydiethylacrylamide and polyacryloylpyrrolidine.

6. A method for separating PTH-amino acids characterized by comprising retaining said PTH-amino acids by a stationary phase comprising a chromatographic packing chemically modified with a polyalkylacrylamide having terminal amino, carboxyl, hydroxyl groups or a copolymer of the same; and allowing the PTH-amino acids to pass through a single mobile phase while changing the hydrophilic/hydrophobic balance on the stationary phase surface by the temperature gradient method wherein the external temperature is changed stepwise to thereby separate the PTH amino acids.

7. The method for separating PTH-amino acids as claimed in claim 6, wherein said mobile phase is an aqueous solvent.

* * * * *